United States Patent [19]

Glock et al.

[11] 4,100,272

[45] Jul. 11, 1978

[54] METHOD OF INCREASING THE RESISTANCE OF SWINE TO SWINE DYSENTERY INFECTION

[75] Inventors: Robert D. Glock; Delbert L. Harris; Kent J. Schwartz, all of Ames, Iowa

[73] Assignee: Iowa State University Research Foundation, Inc., Ames, Iowa

[21] Appl. No.: 801,745

[22] Filed: May 31, 1977

[51] Int. Cl.² .............................................. A61K 39/02
[52] U.S. Cl. ...................................................... 424/92
[58] Field of Search .......................................... 424/92

[56] References Cited

PUBLICATIONS

Vet. Bull. 44(9)#4329, (1974) of Hudson et al., British Veterinary Journal, (1974), 130 No. 2, "Swine Dysentery: Failure of an Attenuated Strain of Spirochaete, Given Orally, to Protect Pigs Against Subsequent Challenge".

*Primary Examiner*—Shep K. Rose
*Attorney, Agent, or Firm*—Tilton, Fallon, Lungmus & Chestnut

[57] ABSTRACT

The resistance of swine to swine dysentery infection is increased by parenteral administration of killed cells of a virulent isolate of *Treponema hyodysenteriae*.

6 Claims, No Drawings

METHOD OF INCREASING THE RESISTANCE OF SWINE TO SWINE DYSENTERY INFECTION

GRANT REFERENCE

The invention described herein was made in the course of work under a grant from the Department of Health, Education, and Welfare.

BACKGROUND AND PRIOR ART

An anaerobic spirochete, *Treponema hyodysenteriae*, has been characterized as the primary etiological agent in swine dysentery. Harris, D. L.; Glock, R. D.; Christensen, C. R.; and Kinyon, J. M.: Vet. Med./Small Animal Clin. 67:61 (1972); Taylor, D. J.; and Alexander T. J. L.: Brit. Vet. J. 127:108 (1971). The pathogenesis of the disease has not been completely defined but there is evidence that T. *hyodysenteriae* proliferates in the large intestine of pigs in the presence of other secondary organisms and produces a mucohemorrhagic to necrotic enteritis. Meyer, R. C.; Simon, J.; and Byerly, C. S.: Vet. Pathol. 12:46 (1975). Local invasion of the epithelium and lamina propria has been observed but there is no apparent systemic invasion of the causative organism. Glock, R. D.; and Harris, D. L.: Vet. Med./Small Animal Clin. 67:65 (1972); Harris, D. L.; Glock R. D., Kinyon, J. M.: Intestinal Treponematoses. First Symposium on the Biology of Parasitic Spirochetes (1975). Little is known about the immunology of swine dysentery although resistance to reinfection can be demonstrated in convalescent pigs.

Because of the enteric nature of swine dysentery, it has been believed that effective immunization would involve localized immunity in the large intestine. Oral inoculation of attenuated or non-pathogenic isolates of T. *hyodysenteriae* have therefore been tested. However, results of such tests have been negative; no significant increase in the resistance of the swine to dysentery infection having been obtained. Hudson, M. J., Alexander, T. J. L., Lysons, R. J. and Wellstead, P. D.: Brit. Vet. J. (1974) 139:37.

SUMMARY OF INVENTION

The present invention provides a method of increasing the resistance of swine to swine dysentery infection. The method is practiced by the parenteral administration of a vaccine or bacterin containing as the active immunizing agent killed cells of a virulent isolate of Treponema hyodysenteriae. The vaccine is administered parenteraly, preferably intravenously. The vaccine is preferably given to the swine while they are free from active dysentery infection. By administering at least $1 \times 10^9$ killed cells the resistance of the swine to swine dysentery infection can be significantly increased. Preferably, the parenteral administration of the vaccine is given in a series of doses, at least two doses being given to each animal and each dose comprising at least $5 \times 10^8$ killed cells.

The mechanism of the immunization has not been established. However, partial or complete immunization by the method of this invention can be demonstrated by challenge of the vaccinated swine with oral administration of live virulent T. *hyodysenteriae*. On the basis of the results of the experiments which led to the present invention, it seems probable that systemic immunization is involved, although there is a possibility of simultaneous sensitization of local immune systems by circulating antigens. In retrospect, the explanation of systemic immunization finds support in some prior observations. The lesions of swine dysentery characteristically include prominent evidence of increased vascular permeability as indicated by congestion, edema, ultrastructural vascular lesions, and loss of serum proteins. Accumulation of fibrin in the crypts and lumen of the colon suggest the outpouring of serum proteins with a molecular weight much greater than that of serum globulins. If possible selective forces are ignored, it may be assumed that significant quantitites of serum antibodies may be contained in the products of vascular leakage with resultant permeation of the lamina propria, crypts and luminal surface of the colon.

DETAILED DESCRIPTION

The present invention can be practiced with any virulent isolate of T. *hyodysenteriae*. Attenuated or non-virulent isolates or strains are not desirable. A virulent isolate or strain is one which is capable of producing a typical swine dysentary infection. One suitable isolate has heretofore been identified in the literature as B204. See Kinyon, J. M., and Harris, D. L.: Vet. Rec. (1974): 95:219. Referred to in the same publication is the isolate identified as B234, which can also be used in practicing the present invention. However, type strain B78 (ATCC No. 27164) is not suitable, being non-virulent. Isolates B204 and B234 have been deposited with the American Type Culture Collection; B204 being identified as ATCC No. 31212 and B234 as ATCC No. 31287. It should be understood that these isolates are representative of class of virulent isolates or strains which can be employed.

The T. *hyodysenteriae* cells for preparation of the parenteral vaccine can be cultured using trypticase soy broth (TSB) with 10% (v/v) fetal calf serum (FCS). For example, the inoculated broth can be incubated at 37°-38° C. under an anaerobic atmosphere, such as 50:50 $H_2:CO_2$ or $CO_2$ alone. The gaseous atmosphere should be deoxygenated. For further details, see Kinyon, J. M., and Harris, D. L.: Vet. Rec. (1974): 95:219.

After the fermentation has been completed, the cells can be recovered by centrifugation, then resuspended in a cold aqueous saline solution, such as phosphate-buffered saline (0.01 M), at an approximately neutral pH (pH 7.0-7.2).

The cells are killed by a suitable procedure. Standard killing agents may be used such as formalin or merthiolate. For example, the saline solution in which the cells are resuspended may contain a killing-concentration of formaline, such as 0.2% formalin (v/v). The resuspended cells typically will have a cell concentration of about $1 \times 10^8$ to $5 \times 10^8$ cells per millileter. This cell concentrate comprises the vaccine or bacterin. For immunization of swine with the vaccine of this invention, any of the knonw procedures for parenteral administration can be employed, such as intravenous, intramuscular, or subcutaneous. For routine use by veterinarians, intramuscular injection is preferred. However, the greatest immunization effect is obtainable by intravenous injection. Whatever the parenteral procedure, the cells can be given in the form of killed whole cells. While the cells may be disrupted by sonication, or other procedure, it appears to be most advantageous to employ whole cells.

To increase the resistance of the swine to dysentery infection, at least $1 \times 10^9$ killed cells of a virulent isolate of T. *hyodysenteriae* are administered, and preferably at least $3 \times 10^9$ cells. For example, for intravenous vaccination from about $3 \times 10^9$ to about $6 \times 10^9$ killed whole cells can be given. It is preferable to administer the vaccine in a series of doses. For example, at least two doses may be given to each animal and each dose comprising from 2 to 3 × 10⁹ killed cells.

This invention in its theoretical and practical aspects can be better understood in relation to the following experimental examples.

EXAMPLES

Materials and Methods

Experimental Animals—Sixteen (SPF) pigs from a herd with no history of swine dysentery were placed in isolation units at approximately 4 weeks of age and fed a 16% protein grower ration which contained no antibiotics. Rectal swabs were examined by phase-microscopy and found to be free of T. *hyodysenteriae*-like organisms (THLO) during a one-week period of acclimation. Fecal cultures were negative of Salmonella spp.

Vaccine Preparation—Cultures of T. *hyodysenteriae* (ATCC No. 31212) were grown for approximately 48 hrs. in aerobically prepared trypticase soy broth with 10% fetal calf serum under deoxygenated $H_2:CO_2$ at 38° C. They were then centrifuged at 10,000 g for 20 minutes and resuspended in cold (4° C.) phosphate-buffered saline (PBS) at pH 7. which contained 0.2% formalin. After a second centrifugation the organisms were again resuspended in cold PBS with 0.2% formalin to a density equal to McFarland nephelometer tube 7. This concentration resulted in a transmittance of 87% at 450 nm on a colorimeter. The completed antigen was stored at 4° C.

Inoculum—Challenge inoculum consisted of the same isolate of T. *hyodysenteriae* grown as described for antigen preparation. Ninety ml of whole culture containing approximately 1 × 10⁸ organisms per ml was administered to each pig via stomach tube on 2 consecutive days following a 24 h period of starvation.

Experimental Design—The 16 pigs were randomly assigned to 6 separate pens. Eight of the pigs in 3 pens were given 6 intravenous injections of formalin-killed T. *hyodysenteriae* at 6-day intervals. The volumes of antigen suspension per pig were successively increased in 0.5 ml increments from 0.5 ml at the first injection. The 8 remaining pigs served as controls.

The challange inoculum was administered to all pigs on the 7th and 8th days the last antigen injection in the principals. Clinical evaluation of response to challenge was recorded for each pig on a daily basis for 30 days post-inoculation (DPI).

Evaluation of Response to Challenge—Each pig was observed daily and 3 clinical parameters were scored on a scale of 1 to 4.

General Condition: 1 = normal; 2 = gaunt, mildly inactive; 3 = very gaunt, rough hair, very inactive, 4 = emaciated, moribund.

Feces Consistency: 1 = normal, firm; 2 = soft, not formed; 3 = liquid; 4 = watery.

Feces Composition: 1 = normal; 2 = increased mucus; 3 = increased mucus, small flecks of blood; 4 = large amount of blood present.

For purposes of tabulation, a score of 3 or 4 was considered to be respectively cachexia, diarrhea and dysentery in the 3 parameters observed.

A daily index for each pig was calculated as the mean of the scores for the 3 individual observations. Pigs that died were given the maximum score of 4 for each of the parameters through the remainder of the study for purposes of analysis.

A rectal swab from each pig was placed in 0.5 ml of PBS each day. A drop of the resulting suspension was observed by phase-contrast microscopy (400X) and the number of THLO per field was estimated. Isolation of Salmonella spp. was attempted on pooled rectal swabs from each pen prior to challenge and weekly thereafter.

Necropsy Procedures—A necropsy was performed on each pig that died during the trial. Macroscopic lesions were recorded and scrapings of the colonic mucosa were observed by phase-contrast microscopy for the presence of THLO. Salmonella isolations were attempted from liver, spleen, mesenteric lymph node, and colon.

Serology—Serum was collected from each pig prior to the first injection of antigen, immediately before oral challenge and 30 days post-challenge. Antibody titers against T. *hyodysenteriae* were determined by the indirect fluorescent antibody technique.

Wells were formed on glass microscope slides by placing 4 separate drops of glycerol on each slide, spraying with a fluorocarbon dry-film lubricant ("Fluoroglide", Chemplast, Inc., Wayne, N.J.), rinsing the glycerol off with hot tap water, and drying. A .025 ml quantity of T. *hyodysenteriae* antigen was diluted 1:10, spread in each well, allowed to dry, and fixed for 5 minutes in acetone at 4° C.

Serum dilutions were prepared using microtiter techniques to attain twofold dilutions from 1:10 through 1:640. A drop (.05 ml) of each dilution was added to one of the antigen wells and incubated at 37° C. in a moist chamber for 30 minutes. After two 10 minute washes in PBS, 0.025 ml of fluorescein isothiocyanate labeled IgG fraction of rabbit and anti-porcine IgG (Miles Laboratories, Inc., Kankakee, Ill.) was added to each well and incubated at 37° C. in a moist chamber for 30 minutes. Slides were then washed 2 times in PBS for 10 minutes and once for 30 minutes. They were examined with a microscope utilizing an ultraviolet light source. A positive reaction was regarded as a well in which a majority of the T. *hyodysenteriae* fluoresced.

The data is set out below in Tables 1, 2 & 3.

Table 1

Mean Values of Clinical Responses in Pigs Inoculated Intragastrically with T. *hyodysenteriae*

| Clinical Response | Controls n=8 | Immunized n=8 |
| --- | --- | --- |
| Diarrhea: | | |
| Day of Onset≠ | 6.8 | 18.0** |
| Days Duration | 18.0 | 3.1* |
| Dysentery: | | |
| Day of Onset | 7.4 | 27.4** |
| Days Duration | 14.5 | 0.3* |
| Cachexia: | | |
| Day of Onset | 8.6 | 27.5** |
| Days Duration | 14.9 | 0.1* |
| Combined Index | 2.56 | 1.24** |
| Deaths | 3/8 | 0/8 |

≠Trial terminated at 30 days. Calculations are based on a value of 30 assigned to each pig which remained normal.
*$P < 0.05$
**$P < 0.01$

Table 2

*Treponema hyodysenteriae*-like organisms (THLO) in rectal swabs of immunized and control pigs

| | Immunized | | Control | |
| --- | --- | --- | --- | --- |
| DPI | THLO Observed | <3 THLO/field | THLO Observed | <3 THLO/field |
| 3 | 0/8* | 0/8 | 1/8 | 1/8 |
| 5 | 0/8 | 0/8 | 5/8 | 5/8 |

Table 2-continued

*Treponema hyodysenteriae*-like organisms (THLO) in rectal swabs of immunized and control pigs

| | Immunized | | Control | |
|---|---|---|---|---|
| DPI | THLO Observed | <3 THLO/ field | THLO Observed | <3 THLO/ field |
| 7 | 0/8 | 0/8 | 5/8 | 5/8 |
| 9 | 2/8 | 1/8 | 8/8 | 6/8 |
| 11 | 1/8 | 0/8 | 6/7 | 6/7 |
| 13 | 3/8 | 2/8 | 7/7 | 7/7 |
| 15 | 3/8 | 2/8 | 6/7 | 6/7 |
| 17 | 3/8 | 1/8 | 7/7 | 6/7 |
| 19 | 3/8 | 1/8 | 7/7 | 6/7 |
| 21 | 2/8 | 1/8 | 4/6 | 4/6 |
| 23 | 3/8 | 1/8 | 5/6 | 0/6 |
| 25 | 4/8 | 1/8 | 4/5 | 1/5 |
| 27 | 0/8 | 0/8 | 3/5 | 1/5 |
| 29 | 4/8 | 0/8 | 3/5 | 0/5 |

*numerator = number positive
denominator = number of pigs

Table 3

Serum Antibody Titers Against *T. hyodysenteriae* Determined by Indirect FAT

| | | Titers vs. *T. hyodysenteriae* | |
|---|---|---|---|
| Pen-Pig No. | Pre-Trial | Post Immunization and Pre-Challenge | 30 Days Post-Challenge |
| Immunized | | | |
| 17-83 | ≦10 | 320 | ND |
| 17-93 | ≦10 | 40 | ND |
| 18-96 | ≦10 | 320 | 320 |
| 18-97 | ≦10 | 320 | 320 |
| 18-99 | ≦10 | 320 | 320 |
| 16-13 | ≦10 | 320 | 320 |
| 16-17 | ≦10 | 640 | 160 |
| 16-28 | ≦10 | 640 | 320 |
| | | x̄ 324 | x̄ 251 |
| Controls | | | |
| 17-85 | ≦10 | <10 | ND |
| 17-95 | ≦10 | <10 | ND |
| 18-1 | ≦10 | <10 | 160 |
| 18-98 | ≦10 | 20 | 160 |
| 18-100 | ≦10 | 10 | 80 |
| 16-6 | ≦10 | <10 | ND |
| 16-7 | ≦10 | 10 | 320 |
| 16-20 | ≦10 | 20 | 160 |
| | | x̄ ≦13 | x̄ 110 |

Results

Clinical Signs—Diarrhea was observed in all unvaccinated control pigs. The day of onset ranged from 4 to 13 DPI with a mean of 6.8 DPI and a mean duration of 18.0 days (Table 1). Diarrhea was noted in 6 of 8 vaccinated pigs with onset ranging from 8 to 19 DPI and a mean duration of 3.1 days. Dysentery characterized by blood and mucus in the feces followed the onset of diarrhea in all control pigs with a mean onset of 7.4 DPI and a mean duration of 14.5 days. Dysentery was observed in only one vaccinated pig beginning at 9 DPI and persisting for 2 days.

A generally debilitated condition classified as cachexia followed persistent dysentery in all control pigs but was noted in only one vaccinated pig which improved after one day. A mean daily combined index of 1.24 was calculated for the vaccinated pigs during a 30-day post-challenge observation period (FIG. 1). The score reflected fecal consistency, fecal composition, and general condition based on daily scores ranging from 1 to 4. A comparable index calculated for controls was 2.56. The effects of immunization were also reflected in a mean weight of 48.4 lb. in surviving control pigs compared to a mean weight of 78.8 lb. in immunized pigs.

Fecal Shedding—*Treponema hyodysenteriae*-like organisms were first observed in rectal swabs from control pigs at 3 DPI. Although onset of shedding of THLO was delayed (9 DPI) and numbers of animals shedding was reduced in immunized pigs, it was obvious that immunization did not prevent the establishment of *T. hyodysenteriae* infection which persisted throughout the trial (Table 2). Weekly attempts to isolate Salmonella spp. from pooled rectal swabs from each pen were unsuccessful.

Necropsies—Three control pigs died at 10, 20 and 24 DPI. The 2 which died at 10 and 20 DPI had dysentery for 4 days prior to death. Lesions compatible with swine dysentery 2,14,16 consisted of dehydration and intense inflammation of the large intestine. The mesentery was edematous, and the wall of the colon was hyperemic. The mucosal surfaces of the cecum and colon were swollen and covered by exudate which included mucus, fibrin, and blood. Contents of the large intestine were watery and bloodtinged.

Lesions in the pig which died at 24 DPI were more chronic, reflecting 19 days of dysentery. The wall of the colon was edematous but not hyperemic. Submucosal glands were accentuated and enlarged. The mucosa was covered by a thin, white fibrinous exudate.

Microscopic lesions in all pigs consisted primarily of mucosal edema, dilatation of crypts, and superficial necrosis of the mucosa. Numerous organisms with the appearance of *Balantidium coli* were noted in the exudate adjacent to the mucosa of the pig that died at 24 DPI.

Numerous THLO were present in mucosal scrapings from the cecum and colon of the dead pigs. Attempts to isolate Salmonella spp. from colon, mesenteric lymph node, liver and spleen were negative.

Serology—Serum antibody titers against *T. hyodysenteriae* were 1:10 or less in all pigs at the beginning of the trial. On the day of challenge 6 of the 8 control pigs had titers of 1:10 or less while 2 had titers of 1:20. Titers in immunized pigs at the same time ranged from 1:40 to 1:640 (Table 3) with a mean of 1:324. Titers averaged 1:251 at 30 DPI in immunized pigs while titers in surviving control pigs increased to levels of 1:89 to 1:320 (x = 110).

It will be understood that for commercial practice, a lesser number of injections of the vaccine will be employed than illustrated by the foregoing experimental examples, such as a two-to-three dose administration regimen.

We claim:

1. The method of increasing the resistance of swine to swine dysentery infection, characterized by parenterally administering to swine while free of active swine dysentery infection at least $1 \times 10^9$ killed cells of a virulent isolate of *Treponema hyodysenteriae*.

2. The method of claim 1 in which said swine are administered from $3 \times 10^9$ to $6 \times 10^9$ of said killed cells.

3. The method of claim 1 in which said administered cells are given in a series of doses, at least two doses being given to each animal and each dose comprising, from 2 to $3 \times 10^9$ of said cells.

4. The method of claim 1 in which said isolate of *Treponema hyodysenteriae* is B204 (ATCC No. 31212).

5. The method of claim 1 in which said isolate of *Treponema hyodysenteriae* is B234 (ATCC No. 31287).

6. The method of increasing the resistance of swine to swine dysentery infection, comprising intravenously administering to swine while free of active swine dysentery infection at least $1 \times 10^9$ killed cells of a virulent isolate of *Treponema hyodysenteriae* selected from the class consisting of B204 (ATCC No. 31212) and B234 (ATCC No. 31287).

* * * * *

UNITED STATES PATENT OFFICE
CERTIFICATE OF CORRECTION

Patent No. 4,100,272　　　　　　　　Dated　July 11, 1978

Inventor(s)　Robert D. Glock, Delbert L. Harris and Kent J. Schwartz

It is certified that error appears in the above-identified patent and that said Letters Patent are hereby corrected as shown below:

Column 1, line 6 cancel "Health, Education, and Welfare"

and substitute --Agriculture--.

Signed and Sealed this

*Thirteenth* Day of *November 1979*

[SEAL]

*Attest:*

RUTH C. MASON　　　　　　　　LUTRELLE F. PARKER
*Attesting Officer*　　　　　*Acting Commissioner of Patents and Trademarks*